United States Patent [19]

Zengel et al.

[11] 4,053,510
[45] Oct. 11, 1977

[54] PROCESS FOR THE PRODUCTION OF AROMATIC AND CYCLOALIPHATIC DICARBOXYLIC ACID DIAMIDES

[75] Inventors: Hans Zengel, Kleinwallstadt; Manfred Bergfeld, Erlenbach, both of Germany

[73] Assignee: Akzo N.V., Arnhem, Netherlands

[21] Appl. No.: 537,120

[22] Filed: Dec. 30, 1974

[30] Foreign Application Priority Data

Mar. 6, 1974 Germany .............................. 2410537

[51] Int. Cl.² .......................................... C07C 102/04
[52] U.S. Cl. ............................ 260/557 R; 260/558 A
[58] Field of Search ............ 260/558 R, 557 R, 558 A

[56] References Cited

U.S. PATENT DOCUMENTS

| 1,989,968 | 2/1935 | Bruson | 260/557 R X |
| 2,723,266 | 11/1955 | Lincoln et al. | 260/558 R X |
| 2,849,482 | 8/1958 | Raecke et al. | 260/558 R X |
| 3,607,918 | 9/1971 | Jurewicz | 260/558 A X |

OTHER PUBLICATIONS

Chem. Abs., vol. 77, 1972, p. 342, 125916z, Article by Freidlin, G. N. et al.

*Primary Examiner*—Allen B. Curtis
*Attorney, Agent, or Firm*—Keil, Thompson & Shurtleff

[57] ABSTRACT

A dicarboxylic acid diamides is produced by reacting urea with a terephthalic, isophthalic, 2,6-naphthalene-dicarboxylic or 1,4-cyclohexane-dicarboxylic acid at an elevated temperature of about 30°–200° C. and in a liquid reaction medium consisting essentially of chlorosulfonic acid or an at least 10% by weight oleum. The diamide products are widely used in the preparation of pharmaceuticals and protective agents for plants.

9 Claims, No Drawings

PROCESS FOR THE PRODUCTION OF AROMATIC AND CYCLOALIPHATIC DICARBOXYLIC ACID DIAMIDES

A large number of carboxylic acid amide syntheses are described in Houben-Weyl, Methoden der organischen Chemie, Vol. 8, 1952, pages 653 ff., including for example the elimination of water from the ammonium salt of a carboxylic acid, the reaction of carboxylic anhydrides, esters or chlorides with ammonia and also the partial saponification of nitriles. Some of these preparations are also successfully carried out in the technical production of aromatic dicarboxylic acid diamides.

For example, it is known from British Pat. No. 829,251 that by using a four hour treatment with ammonia and under pressures of 150 – 200 atm., terephthalic acid can be converted into 85% diamide at a temperature of 250° C. and terephthalic acid diethyl ester can be converted into 92% diamide at 280° C. In addition to terephthalic acid diamide, the reaction product further contains among many other impurities both terephthalonitrile (p-phenylene cyanide) and also p-cyanobenzoic acid amide.

The partial saponification of carboxylic acid dinitriles can be carried out according to more recent processes by boiling the nitrile with water in the presence of a nickel catalyst (Kenichi Watanabe, Bull. Chem. Soc. Japan 37 [9] pages 1325–9 [1946]; compare C.A., Vol. 62 [1965], page 2735) or by reaction of the nitrile with at least 80% by weight thereof of formic acid under elevated pressure and at temperatures of about 250° C. in the presence of an inert solvent (German Pat. No. 1,283,220) with very good or practically quantitative yields.

These known processes for the preparation of terephthalic acid diamide are thus recognized as either requiring relatively expensive initial reactants or else as leading to mixtures of reaction products which are extremely difficult to separate.

Still other processes are known in which carboxylic acids are to be reacted with certain amides to form the corresponding carboxylic acid amides. As co-reactants bearing amide groups, the following compounds have been identified as being suitable: urea(Aziz-ur Rahman et al, C.A. 48 [1954] 4437; 50 [1956] 11 954; Hach et al., C.A. 47 [1953] 6902; Benbasat et al., C.A. 60 [1964] 1581; Biazzi et al., C.A. 64 [1966] 6488; Paltin et al., C.A. 63 [1965] 8557); thiourea (Aziz-ur Rahman et al, C.A. 49 [1955] 3806 and 54 [1960] 22 485); sulfonic acid amide (Oxley et al, C.A. 41 [1947] 409); sulfamide (Kirsanov et al., C.A. 48 [1954] 2634); and also amidosulfonic acid (Lazareva et al, C.A. 68 [1968] 48714; Piskov et al, Zh. Prikl. Khim. 46 [1973] 1,220–21).

The amidation using sulfamide, sulfonic acid amide or amidosulfonic acid is of interest only as a laboratory preparation and not a large scale technical or industrial process for economical reasons. Also, the syntheses with urea or thiourea have not found any acceptance as industrial processes; according to the known processes using these compounds, the carboxylic acid and urea or thiourea are mixed with each other and heated for several hours at temperatures of 150° C. in the absence of any solvent. The yields are very low, especially when reacting aromatic carboxylic acids.

It is further known that terephthalic acid diamide can be synthesized by reacting terephthalic acid with the amide of a short-chain carboxylic acid, e.g. acetamide, or with a short-chain nitrile, e.g. acetonitrile. The reaction takes place at temperatures of 25° to 100° C. in oleum. With a reaction time of 3 hours, yields of 90 to 95% of theory are obtained.

It is an object of the present invention to provide a more advantageous method of synthesizing a number of aromatic dicarboxylic acid diamides and also 1,4-cyclohexane-dicarboxylic acid diamide, using relatively inexpensive initial materials and proceeding with high selectivity and good yields to a readily separable diamide product. This desirable advance over the prior art is explained in detail in the following specification.

It has now been found, in accordance with the invention, that the foregoing object is achieved in a process for the production of a diamide of the formula

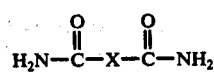

in which X is

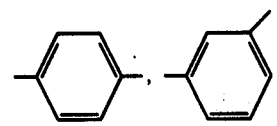

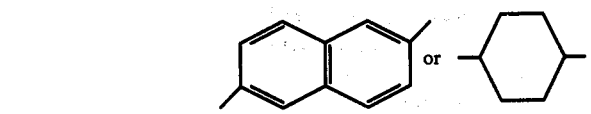

each of which is unsubstituted or substituted by a member selected from the group consisting of alkyl of 1 to 5 carbon atoms, alkoxy of 1 to 5 carbon atoms and halogen, by reacting a dicarboxylic acid of the formula

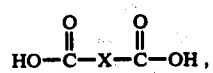

in which X has the same meaning given above, with urea at a temperature of about 30° C. to 200° C. in chlorosulfonic acid or an at least 10% by weight oleum as the reaction medium.

The organic dicarboxylic acids used as initial reactants may contain one or several of the identified substituents, for example up to 4 such substituents and preferably 1–3 substituents, which may be the same or different substituents when using more than one. All of these substituents are essentially inert under the reaction conditions. Of the alkyl substituents, methyl and ethyl are especially preferred. Methoxy and ethoxy are preferred as alkoxy, and chlorine, bromine or iodine are preferred as the halogen substituents.

The amidation of the dicarboxylic acid according to the invention can be interpreted as an irreversible acidolysis of the urea:

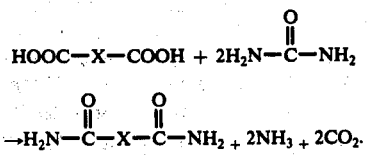

In this reaction, it is assumed that an intermediate carbamic acid arises and is immediately decomposed into ammonia and carbon dioxide.

It was surprisingly found that terephthalic acid, isophthalic acid, 2,6-naphthalene-dicarboxylic acid and 1,4-cyclohexane-dicarboxylic acid as well as their variously nuclear substituted derivatives could be converted into the corresponding dicarboxylic acid diamides by means of the process of the invention with high selectivity as well as good yields. The process of the invention is of especially high technical interest because the dicarboxylic acid diamide being produced is difficultly soluble in cold water and therefore can be separated in a most simple manner by precipitation with water, filtering or centrifuging off the precipitate and then washing with water to remove any adherent sulfuric acid.

The process is equally useful with the four named organic dicarboxylic acids and also their alkyl-, alkoxy- or halogensubstituted derivatives which may be exemplified as follows:

methyl-terephthalic acid;
2-methyl-isophthalic acid;
4-methyl-isophthalic acid;
5-methyl-isophthalic acid;
methoxy-terephthalic acid;
2,5-dimethoxy-terephthalic acid;
ethoxy-terephthalic acid;
2-methoxy-isophthalic acid;
4-methoxy-isophthalic acid;
5-methoxy-isophthalic acid;
chloroterephthalic acid;
2,5-dichloro-terephthalic acid;
tetrachloro-terephthalic acid;
bromo-terephthalic acid;
2,5-dibromo-terephthalic acid;
tetrabromo-terephthalic acid;
5-chloro-2-bromo-terephthalic acid;
iodo-terephthalic acid;
2,5-diiodo-terephthalic acid;
tetraiodo-terephthalic acid;
4-chloro-isophthalic acid;
5-chloro-isophthalic acid;
4,6-dichloro-isophthalic acid;
2,4,6-trichloro-isophthalic acid;
tetrachloro-isophthalic acid;
4-bromo-isophthalic acid;
4,6-dibromo-isophthalic acid;
tetrabromo-isophthalic acid;
4-iodo-isophthalic acid;
5-iodo-isophthalic acid;
tetraiodo-isophthalic acid;
cis- and trans-1-bromo-cyclohexane-dicarboxylic acid-(1,4);
2-bromo-trans-cyclohexane-dicarboxylic acid-(1,4);
1,2-dibromo-cyclohexane-dicarboxylic acid-(1,4);
1,4-dibromo-trans-cyclohexane-dicarboxylic acid-(1,4);
and 2,3-dibromo-cyclohexane-dicarboxylic acid-(1,4).

With the above-named dicarboxylic acids and their derivatives bearing inert substituents, the nuclear sulfonation expected as a side reaction plays no role or only a very minor or subordinate role. In some cases, as for example with the terephthalic acid and the 2,6-naphthalene-dicarboxylic acid, the sulfonation is hindered by reason of the electron distribution of the ring system. In other cases, e.g. with the isophthalic acid, the amidation reaction proceeds substantially more rapidly than the nuclear sulfonation.

The reaction of the named dicarboxylic acids with urea is carried out in accordance with the process of the invention in an homogeneous phase since the reaction products as well as the reactants are soluble in chlorosulfonic acid and in oleum. The course of the amidation reaction is influenced by the reaction temperature, the concentrations or proportions of the substances in the initial reaction mixture and also the reaction temperature. These factors are explained in greater detail as follows.

When using oleum in the process of the invention, a certain minimum concentration is essential for the amidation. As a rule, this minimum oleum concentration falls in a range of about 10 to 20% by weight, i.e. ordinarily around 15% by weight. This percentage by weight of oleum is expressed in conventional manner, representing the amount of $SO_3$ in concentrated $H_2SO_4$. If a less concentrated oleum is used, the reaction either fails to start or else begins only very gradually. Above the designated minimum oleum concentration of at least about 10–20% by weight, the rate of the reaction increases with the oleum concentration. For example, the reaction of terephthalic acid at 80° C. is completed after only one minute when using 50% oleum and after 5 minutes when using 30% oleum. An oleum concentration above about 60% is ordinarily not required, and it is preferred to work in a range of about 30 to 50% with outside limits of about 15 to 60%.

The reaction temperature also has a certain influence on the course of the amidation. When using chlorosulfonic acid or a highly concentrated oleum, e.g. about 60% oleum, the reaction is initiated at about 30° C. With 30% oleum, the reaction begins at about 60° to 70° C. As the temperature is increased, the reaction speed also increases strongly. The end of the upper temperature range for purposes of this invention is generally governed by the stability of the reactants and the reaction products in chlorosulfonic acid or oleum as the reaction medium. With the proposed compounds, this upper limit usually lies in a range of about 150° C. to 200° C.

The reaction of the invention may be generally carried out at about 30° – 200° C., and preferably 60° – 150° C. However, it is most preferably carried out at a temperature of about 80° – 100° C.

The reactants are preferably brought together in stoichiometric amounts, i.e. two mols of urea per mol of the dicarboxylic acid. The use of an excess of either the dicarboxylic acid or the urea has no special influence on the selectivity of the amidation reaction, and for this reason as well as simple economics, such an excess of either reactant is preferably avoided. An excess of the dicarboxylic acid would also tend to create difficulties in working up the reaction mixture for separation of the desired product.

The chlorosulfonic acid or oleum is used in a wide range of amounts of approximately 300 to 3,000% by weight with reference to the dicarboxylic acid, i.e. in a proportion of about 3X to 300X the weight of the organic dicarboxylic acid reactant. Chlorosulfonic acid is most preferably used in an amount of 500 to 1,500% by weight while the oleum in a 10 – 50% concentration (with reference to its $SO_3$ content) is also used in this preferred amount of about 500 to 1,500% by weight, this percentage of the total amount of chlorosulfonic acid or oleum being with reference to the amount of the dicarboxylic acid.

The amidation occurs very rapidly in the process of the invention. In the reaction of terephthalic and isophthalic acid, for example, it is completed after only a few minutes.

The process according to the invention is advantageously carried out in the following manner. First, about 50% of the total amount of chlorosulfonic acid or oleum being used is heated up to the reaction temperature. The dicarboxylic acid reactant is then dissolved in this portion of the heated reaction medium while the urea is dissolved in the remaining portion of chlorosulfonic acid or oleum. The urea solution is then heated up to at least about 30° C. and preferably at least 60° C., after which the two separate solutions are rapidly mixed together. Upon completion of the reaction, the reaction mixture is poured with mixing into an ice/water mixture. The dicarboxylic diamide products are difficulty soluble in the resulting dilute sulfuric acid so that they immediately precipitate out and can be filtered off. With complete transformation or conversion, the dicarboxylic diamides are obtained in high purity as well as practically quantitiative yields.

When using chlorosulfonic acid as the reaction medium, there is another technically interesting alternative for the separation of the dicarboxylic acid. In this instance, the chlorosulfonic acid is first distilled off upon completion of the reaction, preferably under a vacuum. The residue is then washed free of acid while being cooled with water.

The process of the invention makes it possible to convert the named organic dicarboxylic acids into the corresponding diamides in a relatively simple and effective manner. In comparison to known processes which are based upon the reaction of a dicarboxylic acid with an amide, the process according to the present invention is distinguished by its higher yields and selectively and especially by its very short reaction times. Aside from these results, urea is cheaper than the carboxylic acid amides normally used as the amide reactant in prior processes.

The diamides obtained by the present invention are generally known intermediate products havng a wide range of utility, including reaction with a glycol such as ethylene glycol to form a polymer while splitting off ammonia (U.S. Pat. No. 2,914,553), as well as in the syntheses of pharmaceuticals and plant protection agents.

The process of the invention is further illustrated by but not restricted to the following examples. The percentage by weight of the oleum reaction medium is based upon the weight of $SO_3$ in the concentrated sulfuric acid as indicated above.

EXAMPLES 1 - 4

In these examples, the reaction was carried out in a glass flask equipped with a mixer and a thermometer. Above 50% of the total amount of oleum was first placed in the flask and heated to 80° C., after which terephthalic acid was dissolved therein. Urea was next dissolved in the remaining 50% of the oleum, the resulting solution heated to 60° C. and then rapidly mixed with the terephthalic acid solution in the flask. The reaction began immediately. After completion of the reaction, the reaction mixture was poured from the flask into an ice/water mixture while further mixing. The terephthalic acid diamide thereby settled out as a white precipitate. This diamide product was then filtered off, washed several times with water and finally dried to a constant weight.

The first four examples are summarized in the following table which sets forth the amounts of reactants, the oleum amounts and concentrations, the reaction time and temperature and also the yield obtained in each case. The diamide product obtained in each of these examples was found to be very pure.

TABLE I

| Ex. No. | Terephthalic Acid (Mol) | g | Urea (Mol) | g | Oleum % by wt. (SO$_3$) | g | Reaction Temp. ° C. | Reaction Time Minutes | Yield % of Theory |
|---|---|---|---|---|---|---|---|---|---|
| 1 | 0.06 | 10 | 0.12 | 7.2 | 30 | 300 | 80 | 3 | 99.2 |
| 2 | 0.06 | 10 | 0.12 | 7.2 | 30 | 300 | 80 | 10 | 100.0 |
| 3 | 0.10 | 16.6 | 0.20 | 12 | 30 | 200 | 80 | 5 | 99.7 |
| 4 | 0.10 | 16.6 | 0.20 | 12 | 50 | 200 | 80 | 1 | 100.0 |

EXAMPLE 5

An 80° C. hot solution of 21.6 g (0.1 mol) of 2,6-naphthalene-dicarboxylic acid dissolved in 120 g of 30% by wt. oleum is admixed in the same manner as the first examples above with a 60° C. hot solution of 12 g (0.2 mol) of urea dissolved in 80 g of 30% by wt. oleum. This reaction mixture was stirred for 3 hours at 80° C. and then poured into an ice/water mixture. The 2,6-naphthalene-dicarboxylic acid diamide product precipitated as a fine white precipitate which was then filtered off, washed and dried to constant weight. The yield was practically 100% of theory.

EXAMPLES 6 - 9

In each of the separate examples, one mol of the dicarboxylic acid was dissolved in 120 g of a 30% by wt. oleum heated to 80° C. Thus, the amounts of the dicarboxlic acid required were 17.2 g (0.1 mol) of 1,4-cyclohexane-dicarboxylic acid, 18 g (0.1 mol) of monomethylterephthalic acid, 30.4 g (0.1 mol) of tetrachloro-terephthalic acid and 22.7 g (0.1 mol) of 2,5-dimethoxy-terephthalic acid, in Examples 6, 7, 8 and 9, respectively. These initial heated oleum solutions were then admixed in each case with a 60° C. hot solution of 12 g (0.2 mol) of urea dissolved in 80 g of a 30% by wt. oleumm. The reaction mixture was mixed for about two hours at 80° C., then poured onto the ice/water mixture and worked up to recover the precipitated product in the same manner as in the preceding examples.

The resulting products were analytically pure. The yields obtained in each example were as follows.

Table II

| Ex. No. | Product | Yield % of Theory |
|---|---|---|
| 6 | 1,4-cyclohexane-dicarboxylic acid diamide | 82 |
| 7 | Monomethyl-terephthalic acid diamide | 100 |
| 8 | Tetrachloro-terephthalic acid diamide | 100 |
| 9 | 2,5-dimethoxy-terephthalic acid diamide | 80 |

EXAMPLE 10

In the same apparatus described under Examples 1-4, 12 g (0.2 mol) of urea was dissolved in 100 g of a 30% by weight oleum and heated to 70° C. Then, in a single portion, 16.6 g (0.1 mol) of isophthalic acid were admixed into the initial solution. The isophthalic thus added was dissolved with vigorous mixing within about 30 seconds, whereby the temperature rose to about 80° C. The reaction mixture was then stirred for about another 5 minutes at 80° C. and then poured into an ice-/water mixture. There immediately settled out a fine, white precipitate. This precipitate was quickly filtered off, washed with cold water and dried to constant weight. The resulting isophthalic acid diamide was found to be very pure. The yield amounted to almost 100% of theory.

EXAMPLE 11

In the same general manner described in connection with Examples 1-4, 16.6 g (0.1 mol) of terephthalic acid and 12 g (0.2 mol) of urea were dissolved in 200 g of chlorosulfonic acid and then reacted at 100° C. After the reaction time of 1 hour, the chlorosulfonic acid was evaporated under a vacuum (25 mm. Hg at 80° C.). The remaining residue was then digested with cooling in water and then filtered off. It was then washed three times with about 100 ml. of cold water for each wash. After drying, a very pure terephthalic acid diamide remained in a practically quantitative yield.

Similar results are obtained when using chlorosulfonic acid with the other dicarboxylic acid reactants identified hereinabove although a somewhat higher reaction temperature is usually required than when carrying out the reaction in at at least 10% oleum.

The invention is hereby claimed as follows:

1. A process for the production of a diamide of the formula $$H_2N-\overset{O}{\underset{\|}{C}}-X-\overset{O}{\underset{\|}{C}}-NH_2,$$

in which X is

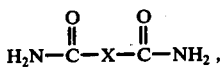, 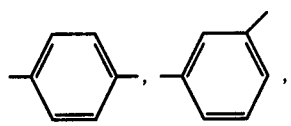,

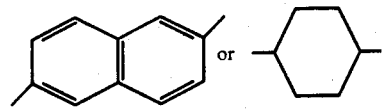 or 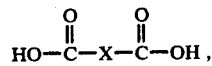

each of which is unsubstituted or substituted by a member selected from the group consisting of alkyl of 1 to 5 carbon atoms, alkoxy of 1 to 5 carbon atoms and halogen, which process comprises:

reacting a dicarboxylic acid of the formula $$HO-\overset{O}{\underset{\|}{C}}-X-\overset{O}{\underset{\|}{C}}-OH,$$

in which X has the same meaning given above, with urea at a temperature of about 60° C to 150° C in chlorosulfonic acid or an at least 10% by weight oleum as the reaction medium.

2. A process as claimed in claim 1 wherein the reaction is carried out at a temperature of about 80° C to 100° C.

3. A process as claimed in claim 1 wherein the oleum has a concentration of about 30 to 50%, based on its SO₃ content.

4. A process as claimed in claim 1 wherein the chlorosulfonic or oleum reaction medium is employed as the reaction medium in an amount of about 300 to 3,000% by weight with reference to the initial dicarboxylic acid.

5. A process as claimed in claim 1 wherein chlorosulfonic acid is employed in an amount of about 500 to 1,500% by weight with reference to the initial dicarboxylic acid.

6. A process as claimed in claim 4 wherein oleum of 10 to 50% concentration, with reference to its SO₃, is employed in an amount of about 500 to 1500% by weight with reference to the initial dicarboxylic acid.

7. A process as claimed in claim 1 wherein the diamide product, upon completion of the reaction, is recovered by precipitation in a cold ice/water mixture and then separating, washing and drying the precipitated material.

8. A process as claimed in claim 1 using chlorosulfonic acid as the reaction medium wherein the diamide product is recovered by distilling off the chlorosulfonic acid under a vacuum.

9. A process as claimed in claim 1 in which the dicarboxylic acid and the urea are reacted in approximately stoichiometric amounts.

* * * * *

UNITED STATES PATENT AND TRADEMARK OFFICE
CERTIFICATE OF CORRECTION

PATENT NO. : 4,053,510
DATED : October 11, 1977
INVENTOR(S) : Hans Zengel and Manfred Bergfeld It is certified that error appears in the above-identified patent and that said Letters Patent are hereby corrected as shown below:

Column 8, line 32, "claim 1" should read --claim 4--.

Signed and Sealed this

Twenty-eighth Day of March 1978

[SEAL]

Attest:

RUTH C. MASON
Attesting Officer

LUTRELLE F. PARKER
Acting Commissioner of Patents and Trademarks